United States Patent
Jee et al.

(10) Patent No.: US 11,065,300 B2
(45) Date of Patent: Jul. 20, 2021

(54) IMMUNOMODULATOR FOR HYPERSENSITIVITY REACTION TO HOUSE DUST MITE-DERIVED ALLERGEN

(71) Applicant: MD HEALTHCARE INC., Seoul (KR)

(72) Inventors: Young Koo Jee, Seongnam-si (KR); Yoon-Keun Kim, Namyangju-si (KR); Hanki Park, Seoul (KR)

(73) Assignee: MD HEALTHCARE INC., Seoul (KR)

( * ) Notice: Subject to any disclaimer, the term of this patent is extended or adjusted under 35 U.S.C. 154(b) by 0 days.

(21) Appl. No.: 16/070,220

(22) PCT Filed: Nov. 4, 2016

(86) PCT No.: PCT/KR2016/012626
§ 371 (c)(1),
(2) Date: Jul. 13, 2018

(87) PCT Pub. No.: WO2017/122915
PCT Pub. Date: Jul. 20, 2017

(65) Prior Publication Data
US 2019/0247465 A1 Aug. 15, 2019

(30) Foreign Application Priority Data

Jan. 15, 2016 (KR) .................. 10-2016-0005094
Nov. 3, 2016 (KR) .................. 10-2016-0145662

(51) Int. Cl.
| | |
|---|---|
| *A61K 38/17* | (2006.01) |
| *A61P 37/08* | (2006.01) |
| *A61P 11/06* | (2006.01) |
| *A61K 39/35* | (2006.01) |
| *A61K 9/00* | (2006.01) |
| *A61K 9/127* | (2006.01) |
| *A61K 35/74* | (2015.01) |
| *A61K 39/00* | (2006.01) |

(52) U.S. Cl.
CPC ........ *A61K 38/1767* (2013.01); *A61K 9/0019* (2013.01); *A61K 9/0043* (2013.01); *A61K 9/127* (2013.01); *A61K 35/74* (2013.01); *A61K 39/35* (2013.01); *A61P 11/06* (2018.01); *A61P 37/08* (2018.01); *A61K 2039/523* (2013.01); *A61K 2039/55555* (2013.01); *A61K 2039/57* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 8,163,295 | B2* | 4/2012 | Bos | A61P 31/04 424/249.1 |
| 2005/0013831 | A1 | 1/2005 | Foster et al. | |
| 2015/0231232 | A1* | 8/2015 | Grandi | A61K 39/092 424/244.1 |
| 2016/0375121 | A1* | 12/2016 | Bailey | A61K 39/12 424/199.1 |

FOREIGN PATENT DOCUMENTS

| | | | |
|---|---|---|---|
| JP | 2005-514388 A | 5/2005 | |
| JP | 2007-534667 A | 11/2007 | |
| JP | 2008-519776 A | 6/2008 | |
| JP | 2013-507354 A | 3/2013 | |
| JP | 2013-534830 A | 9/2013 | |
| JP | 2015-57393 A | 3/2015 | |
| JP | 2015-164424 A | 9/2015 | |
| KR | 10-2011-0038575 A | 4/2011 | |
| WO | WO 1993/14115 * | 7/1993 | C07K 5/04 |
| WO | 2005/079854 A1 | 9/2005 | |
| WO | 2013/151706 A2 | 10/2013 | |

OTHER PUBLICATIONS

Kurucz et al. 'Current Animal Models of Bronchial Asthma.' Curr. Pharm. Des. 12:3175-3194, 2006.*
Mukherjee et al. 'Allergic Asthma: Influence of Genetic and Environmental Factors.' J. Biol. Chem. 286(38):32883-32889, 2011.*
Ichikawa et al. 'Solution Structure of Der f 2, the Major Mite Allergen for Atopic Diseases.' J. Biol. Chem. 273(1): 356-360, 1998.*
Acevedo et al. 'Bacterial outer membrane vesicles and vaccine applications.' Front. Immunol., Mar. 24, 2014 | https://doi.org/10.3389/fimmu.2014.00121.*
Cooperstock et al. 'Polymyxin B Inactivation of Lipopolysaccharide in Vaccines of Gram-Negative Bacteria.' Infection and Immunity 33(1):315-318, 1981.*
Kim et al., "Extracellular vesicle-derived protein from Bifidobacterium longum alleviates food allergy through mast cell suppression", J. Allergy Clin. Immunol., vol. 137, No. 2—18 pages, (Feb. 2016).
Kim et al., "*Staphylococcus aureus*-derived extracellular vesicles induce neutrophilic pulmonary inflammation via both Th1 and Th17 cell responses", Allergy, vol. 67—11 pages, (2012).
Kim et al., "Extracellular Vesicles Derived from Gram-Negative Bacteria, such as *Escherichia coli*, Induce Emphysema Mainly via IL-17A-Mediated Neutrophilic Inflammation", The Journal of Immunology, vol. 194—10 pages, (2015).

(Continued)

*Primary Examiner* — Nora M Rooney
(74) *Attorney, Agent, or Firm* — Knobbe Martens Olson & Bear LLP

(57) ABSTRACT

The present invention relates to an immunomodulator for the prevention or treatment of an allergic disease caused by house dust mite-derived allergens. Particularly, the present invention provides an immunomodulatory pharmaceutical composition comprising as an effective ingredient a bacteria extracellular vesicle containing an allergens derived from North American house dust mite or European house dust mite, and a preparation method therefor.

17 Claims, 16 Drawing Sheets

Specification includes a Sequence Listing.

(56) References Cited

OTHER PUBLICATIONS

Park et al., "House Dust Mite Allergen Der f 2-induced Phospholipase D1 Activation is Critical for the Production of Interleukin-13 through Activating Transcription Factor-2 Activation in Human Bronchial Epithelial Cells", The Journal of Biological Chemistry, vol. 284, No. 30—12 pages, (Jul. 24, 2009).

Bobbins et al., "Regulation of Immune Responses by Extracellular Vesicles", Nat. Rev. Immunol., vol. 14, No. 3—28 pages, (Mar. 2014).

Sohn et al., "A Survey of House Dust Mite Allergen Contamination in House", Journal of Korean Society for Atmospheric Environment, vol. 22, No. 5—5 pages, (2006).

International Search Report of Patent Application No. PCT/KR2016/012626 which is the parent application and its English translation—8 pages, (dated Feb. 24, 2017).

Acevedo et al., "Bacterial outer membrane vesicles and vaccine applications", Frontiers in Immunology, vol. 5, No. 121—6 pages (Mar. 24, 2014).

Lin et al., "Prevention and treatment of allergic inflammation by an Fcγ-Der f2 fusion protein in a murine model of dust mite-induced asthma", Immunologic Research, vol. 52, No. 3—8 pages (Apr. 27, 2012).

Supplementary European Search Report in EP Patent Application No. 16885226.7—10 pages. (dated May 28, 2019).

Office Action of European Patent Application No. 16885226.7—4 pages (dated May 27, 2020).

Office Action of Japanese Patent Application No. 2018-536115—9 pages (dated May 21, 2019).

\* cited by examiner

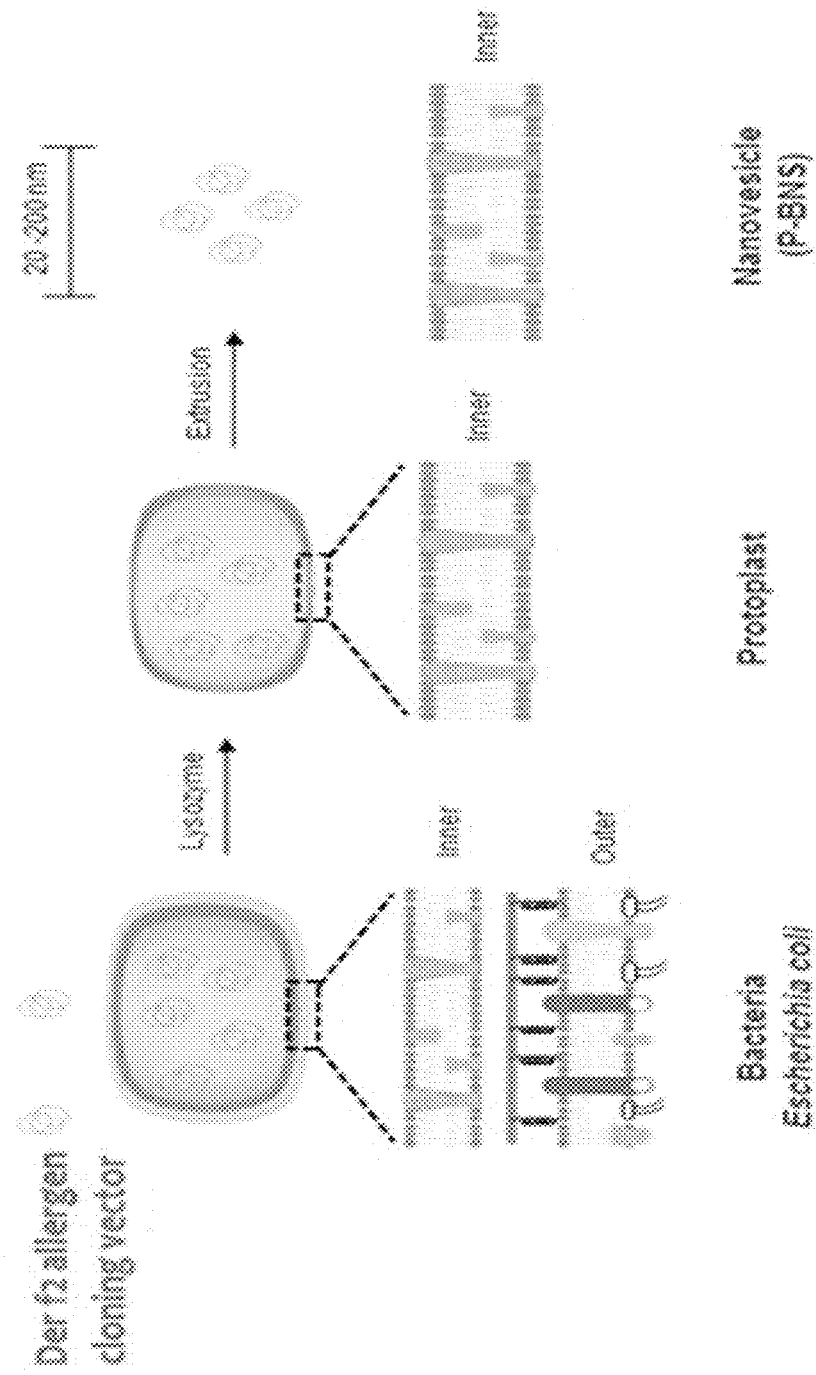
[Fig. 1]

[Fig. 2]
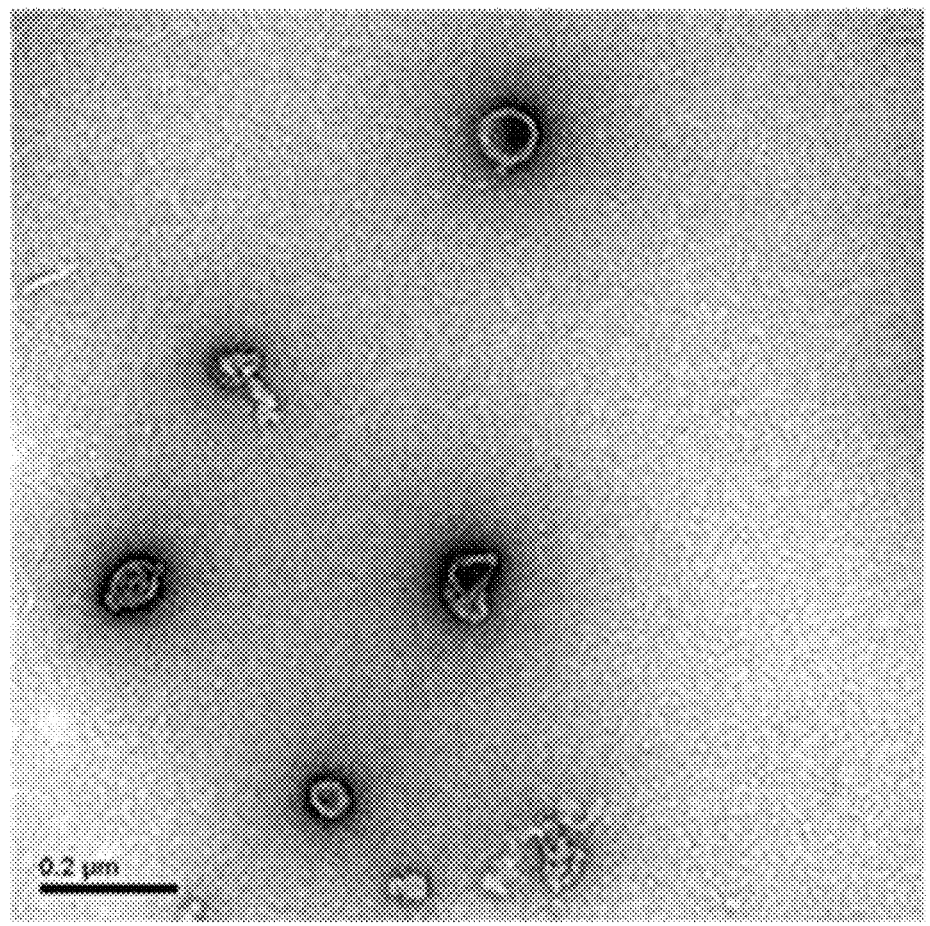

[Fig. 3]
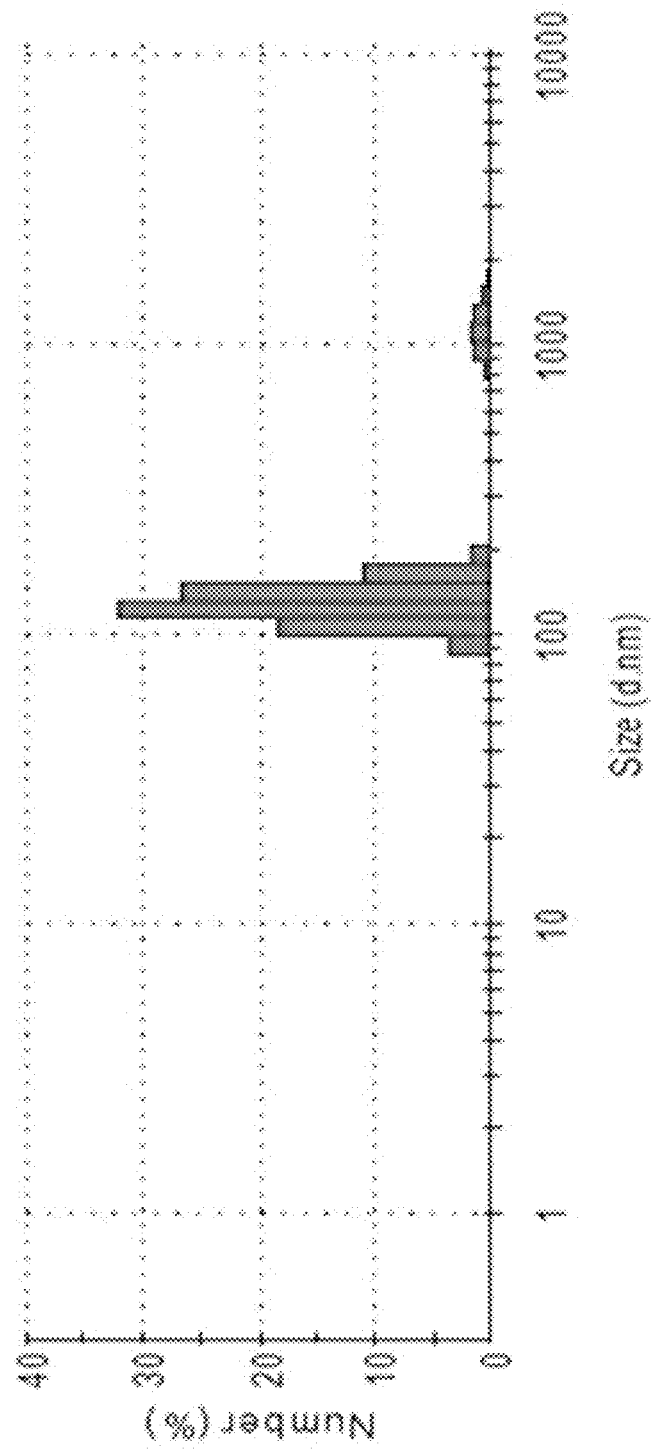

[Fig. 4]
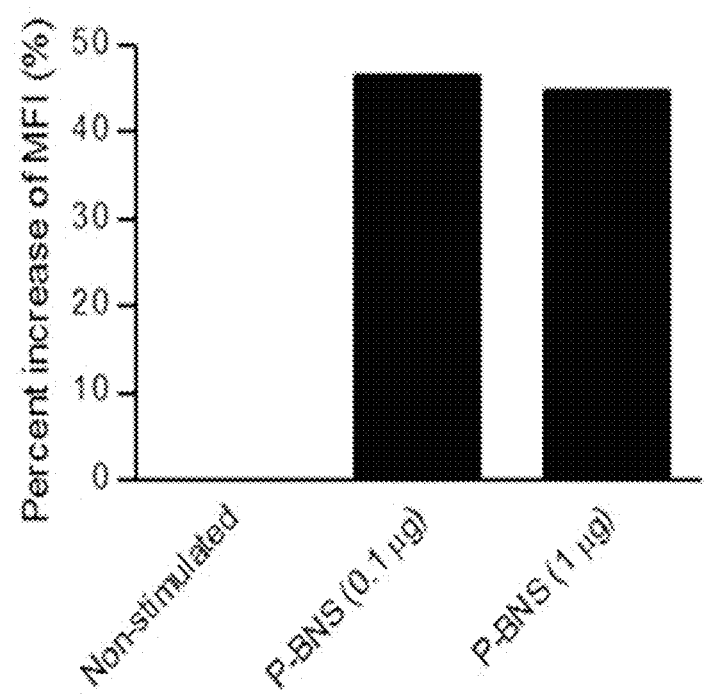

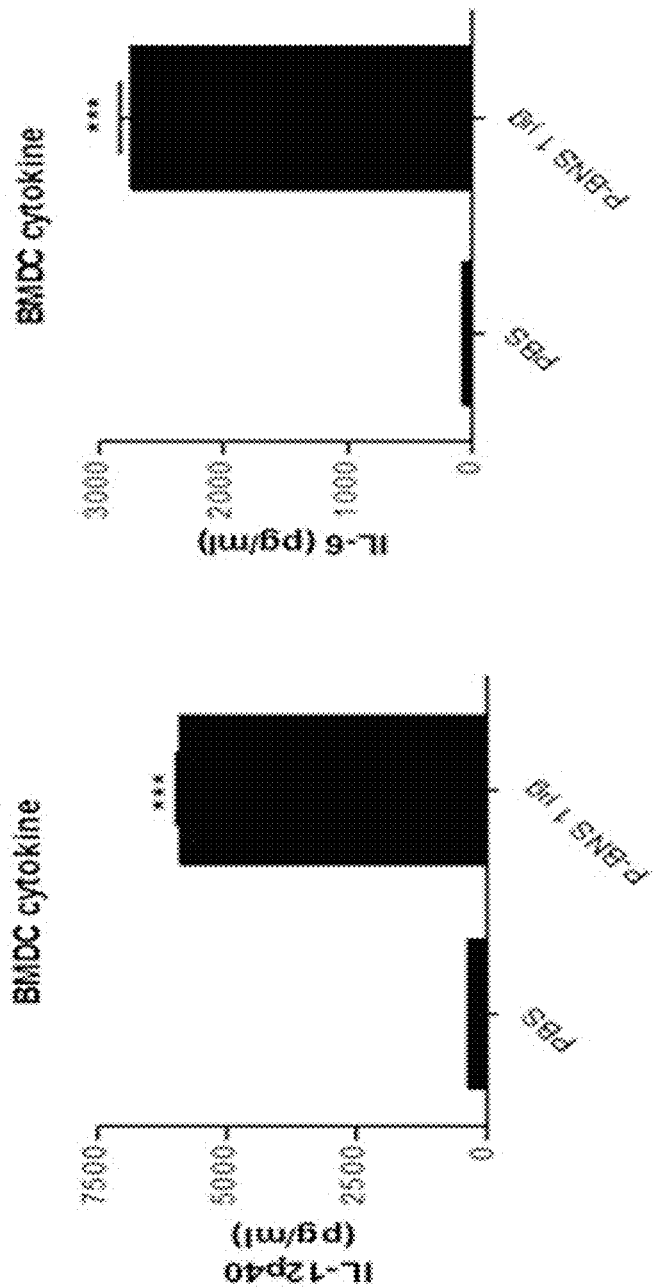
[Fig. 5]

[Fig. 6]
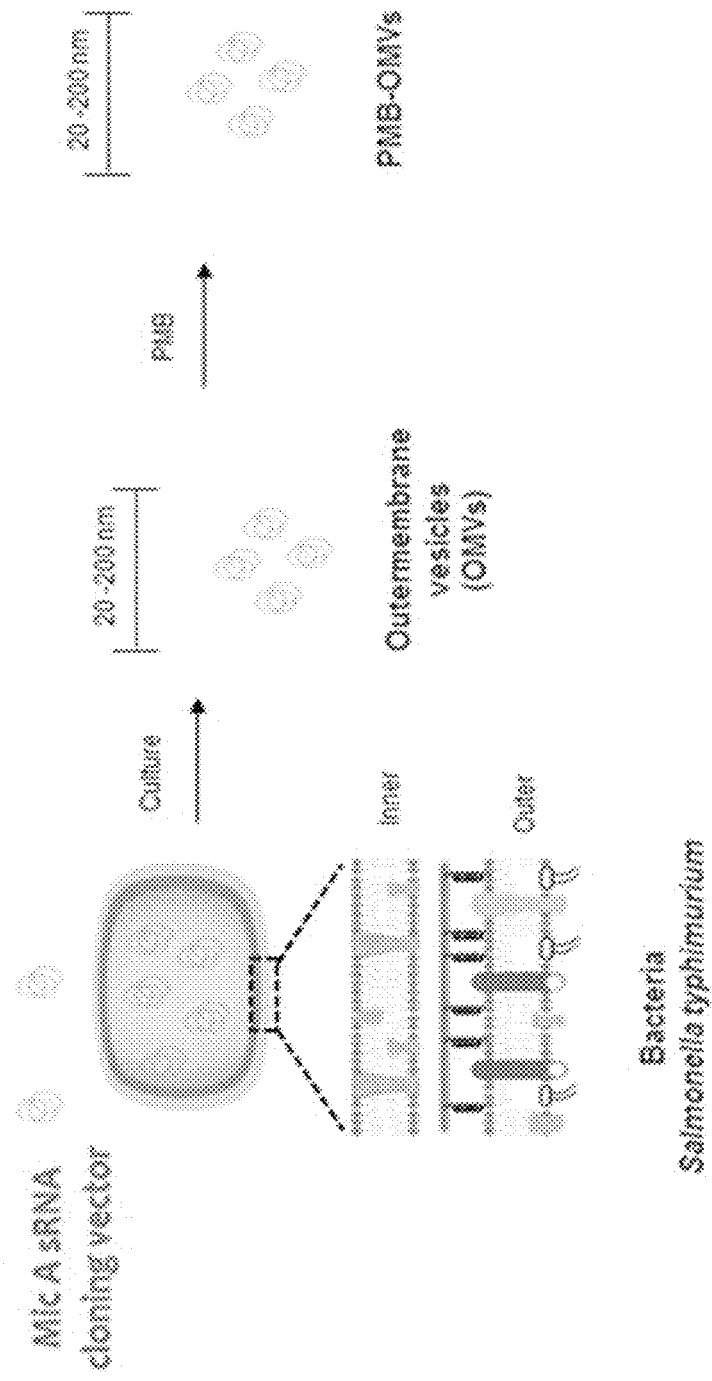

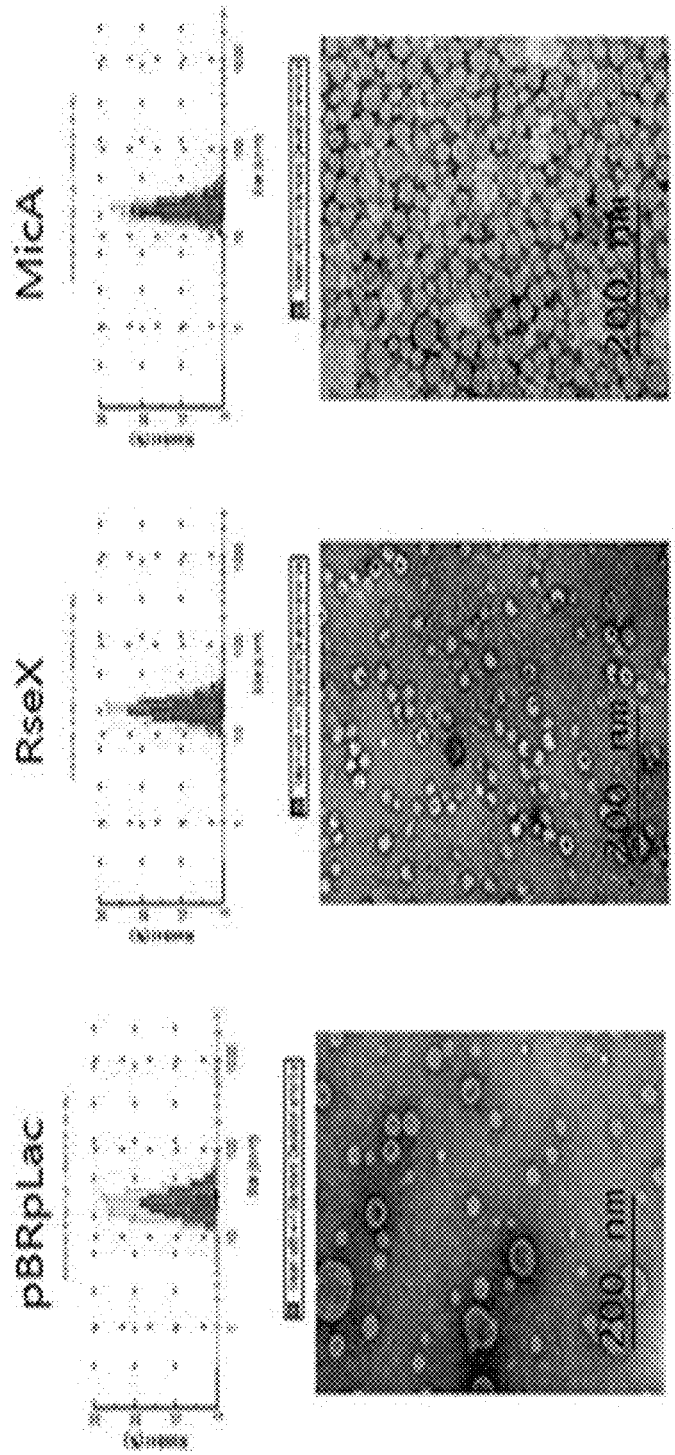
[Fig. 7]

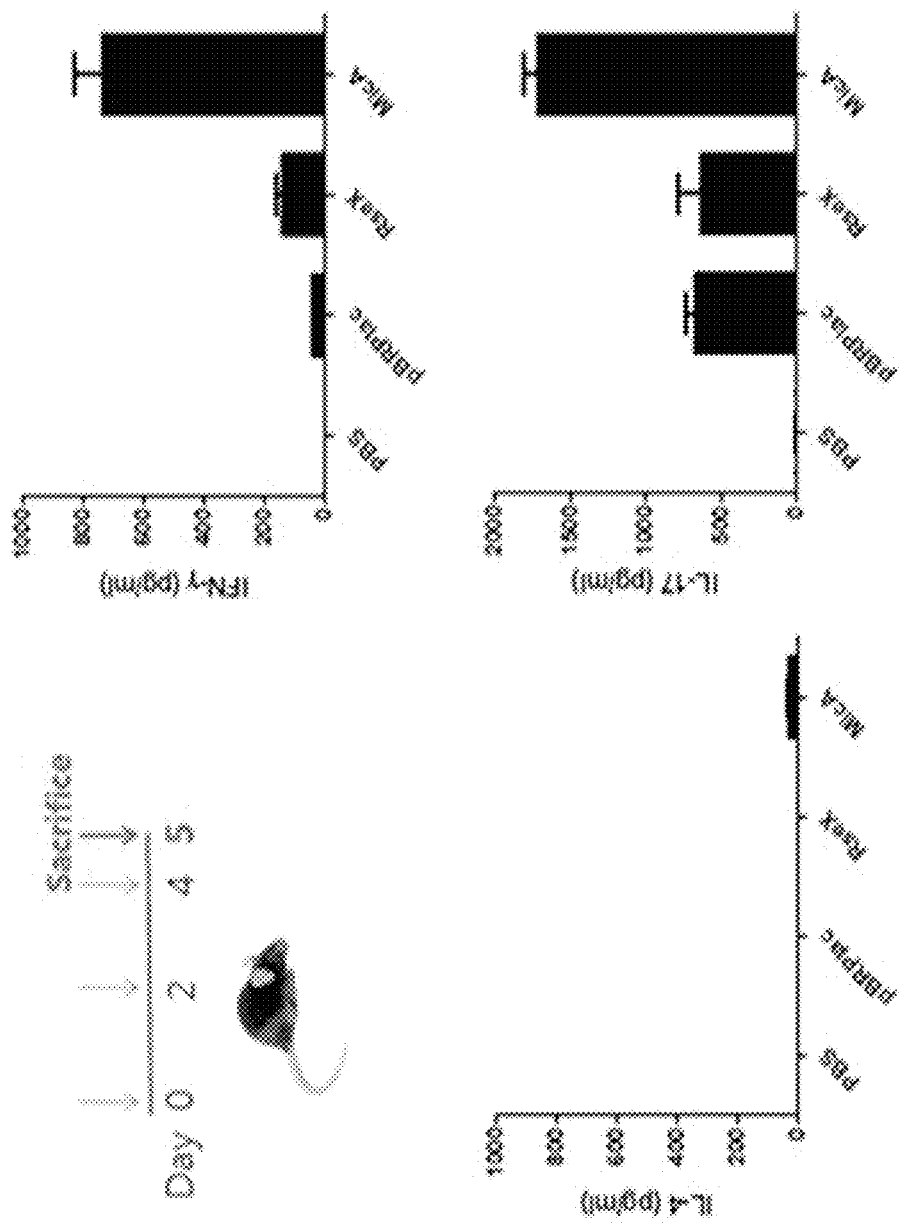
[Fig. 8]

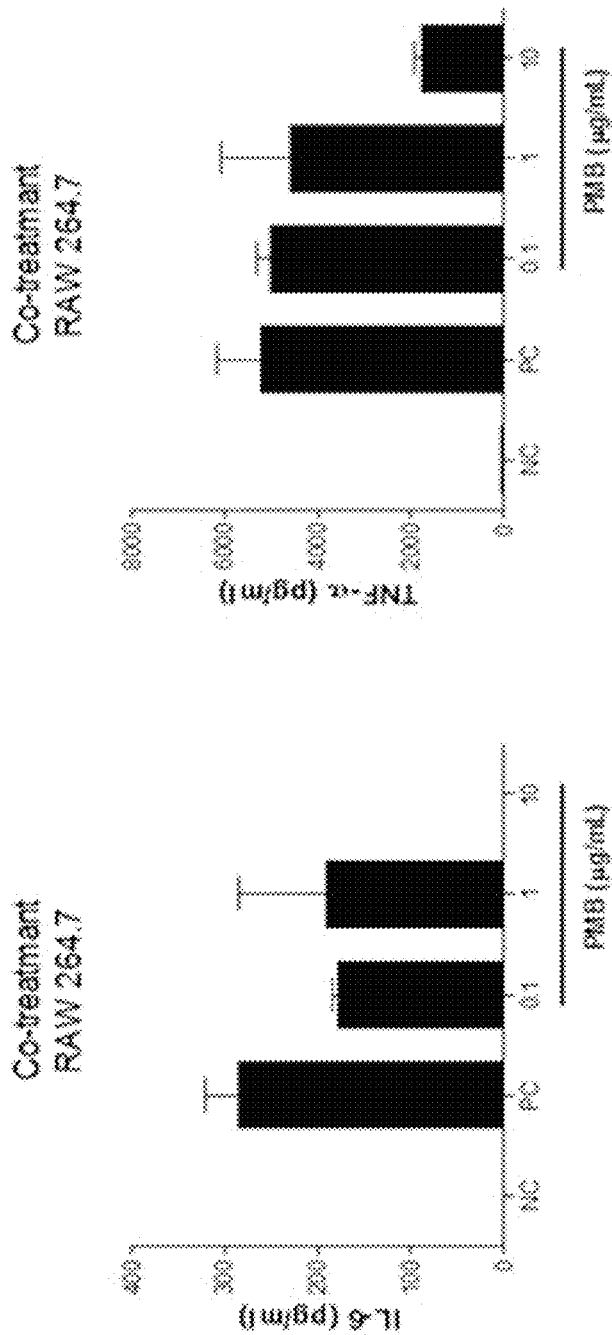
[Fig. 9]

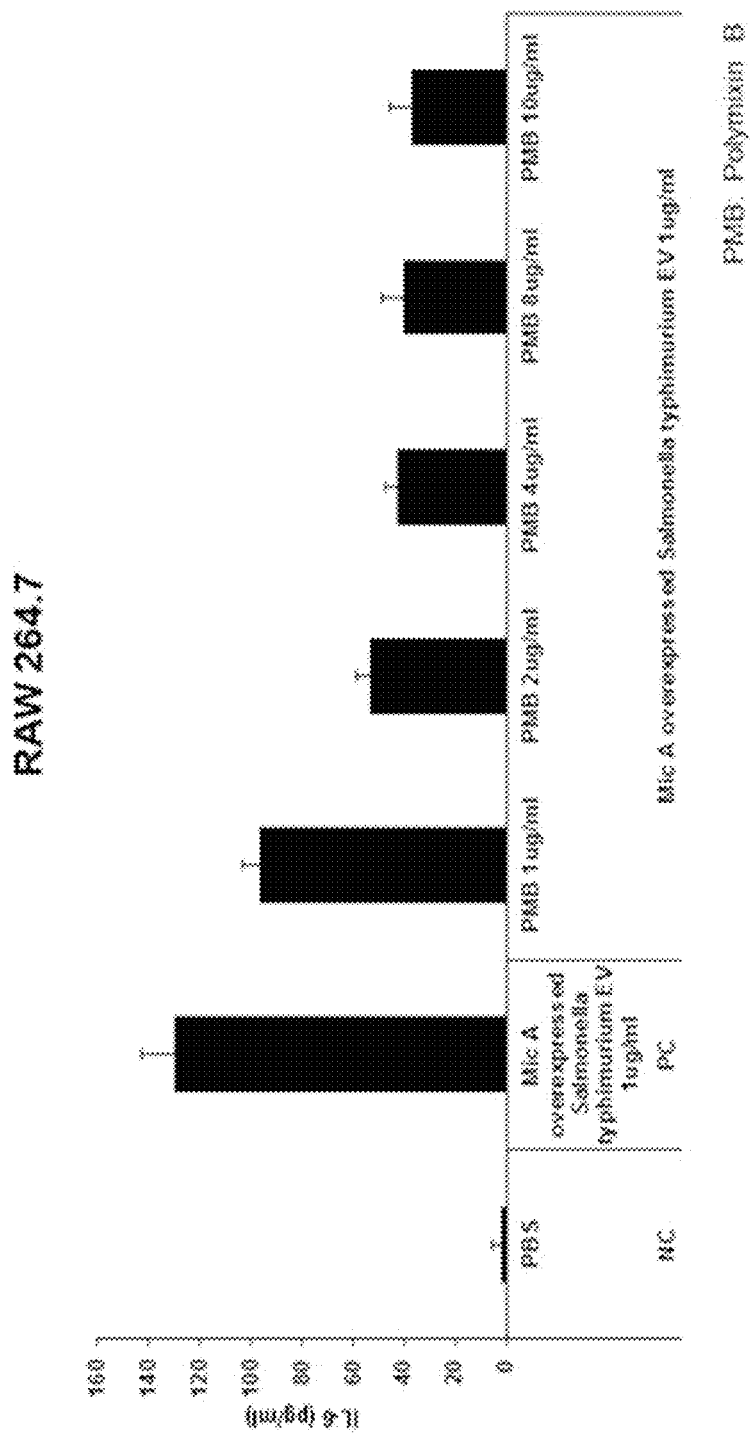

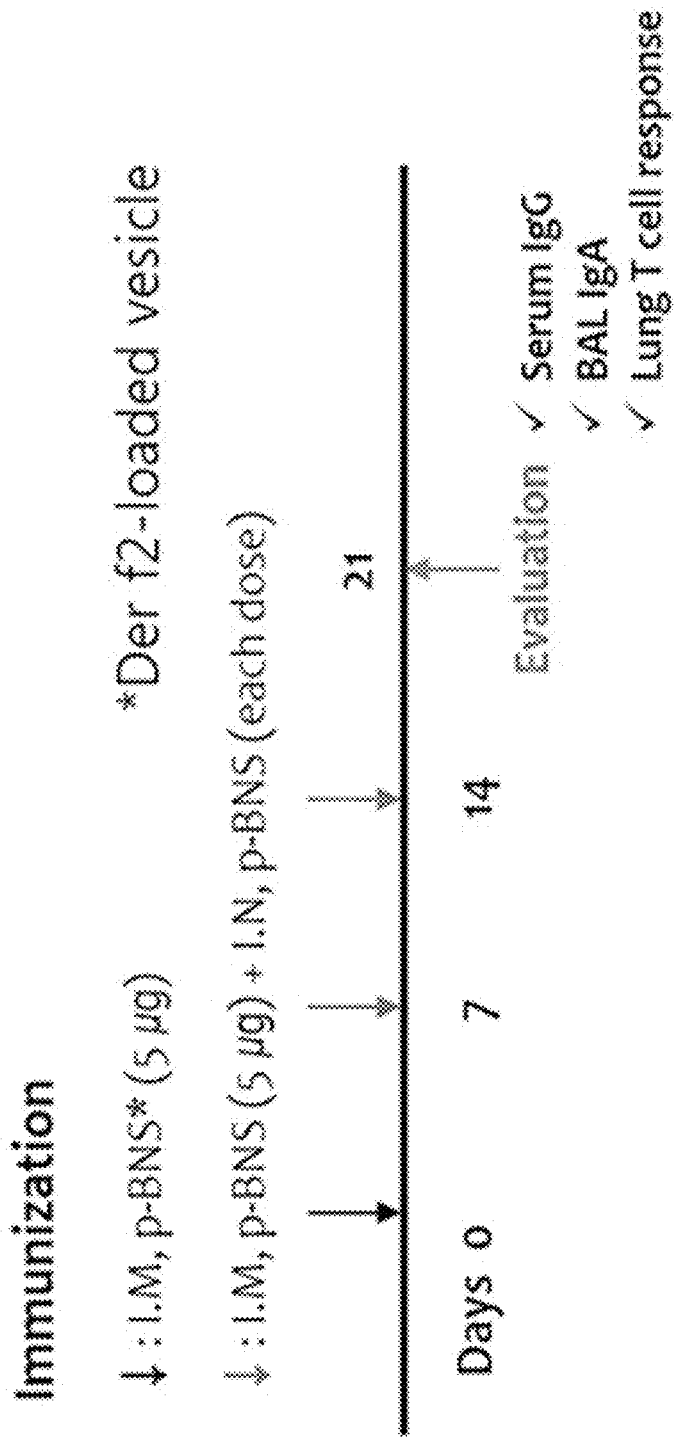
[Fig. 11]

[Fig. 12a]
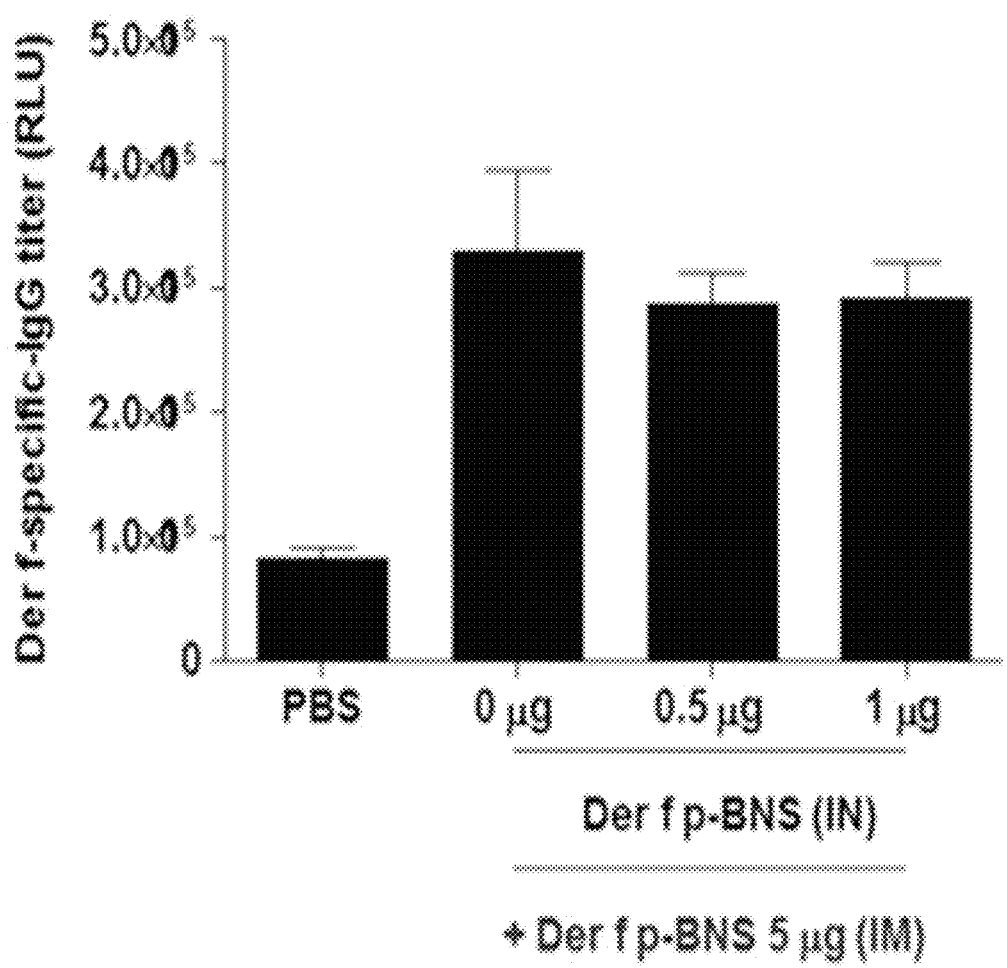

[Fig. 12b]
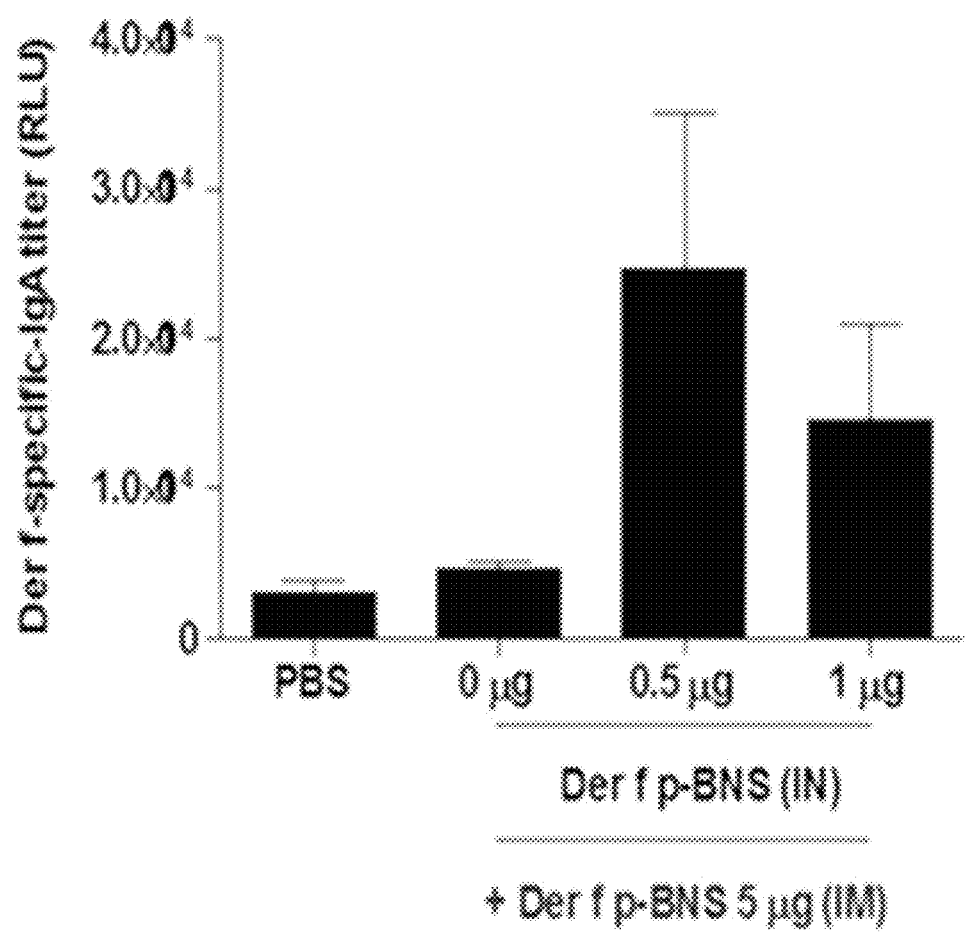

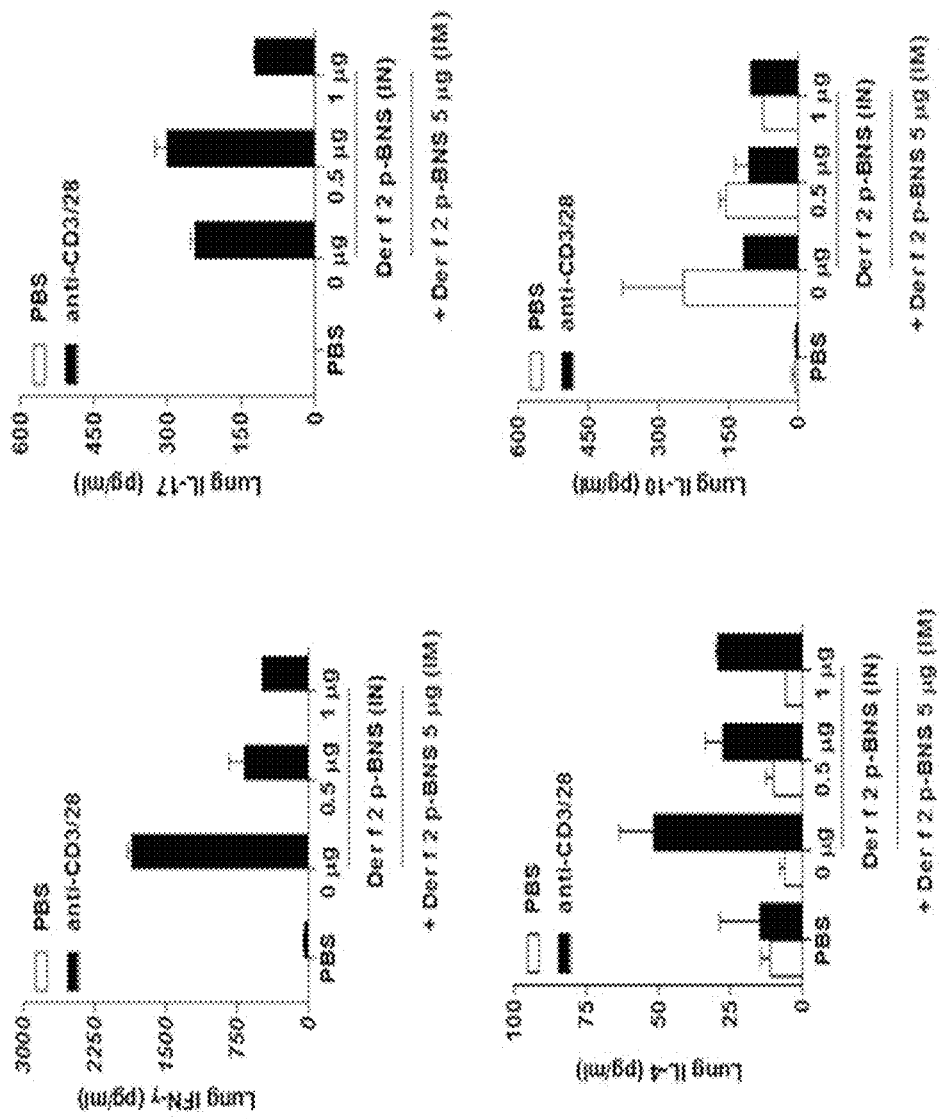
[Fig. 13]

[Fig. 14]
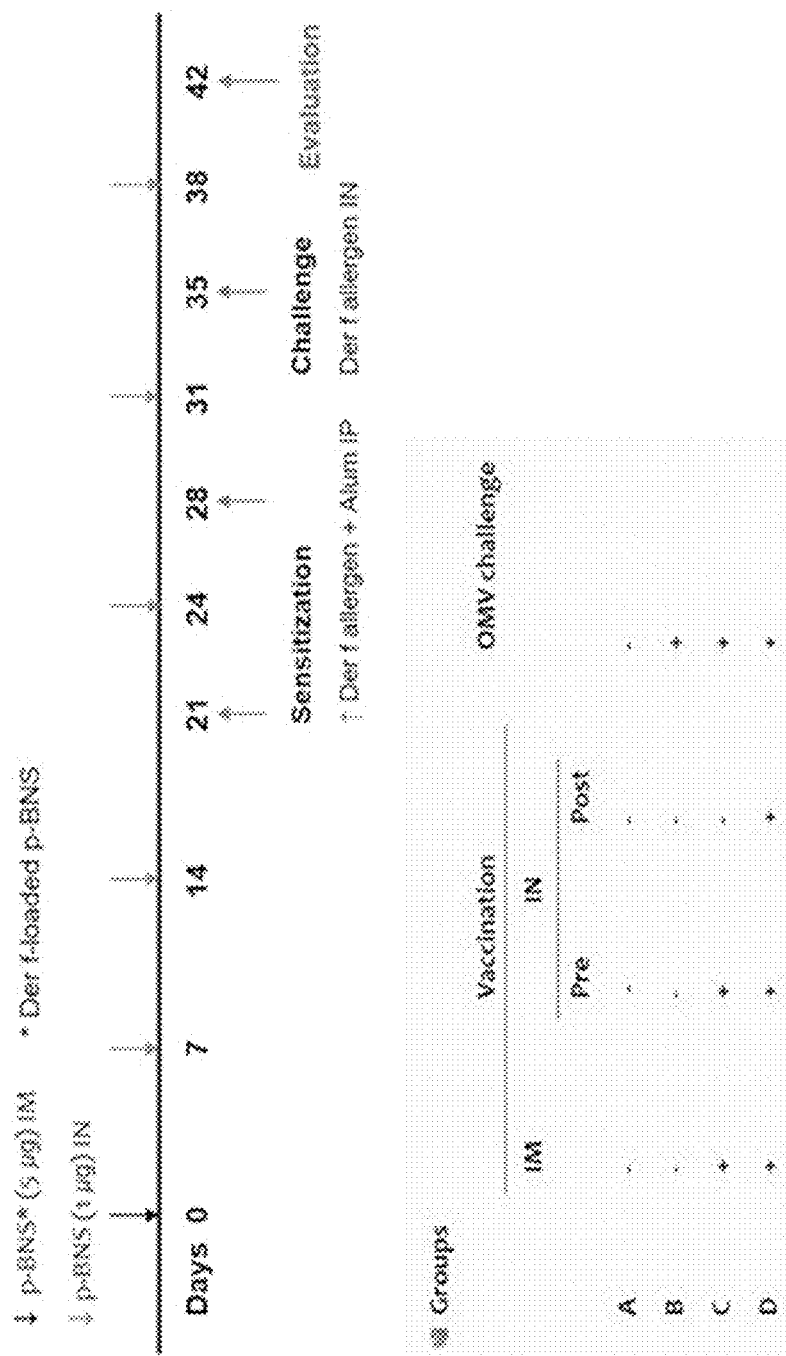

[Fig. 15]
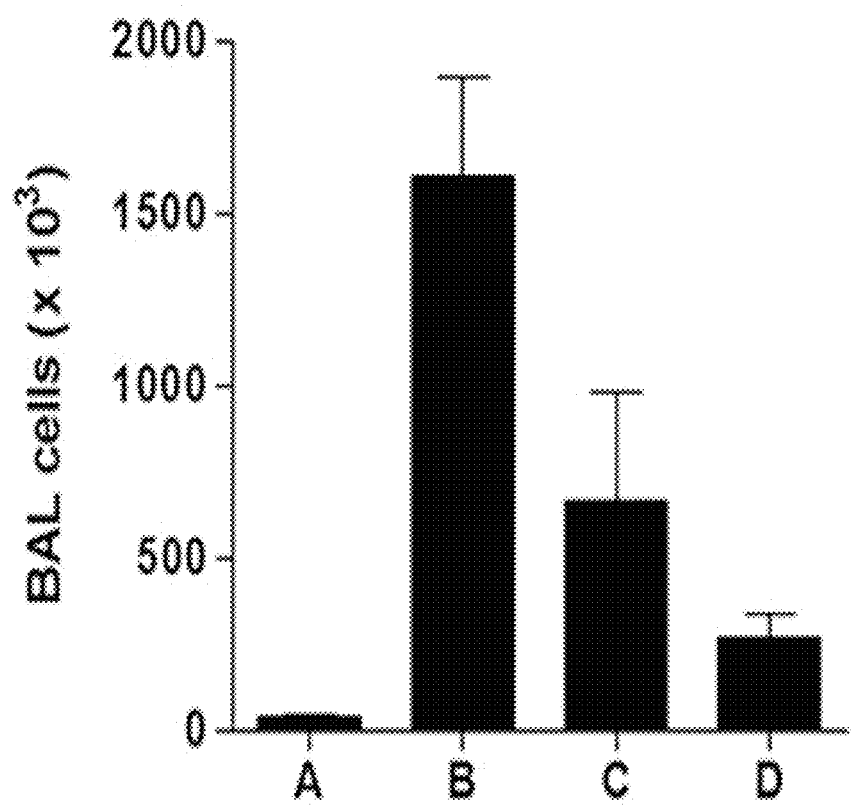

SEQUENCE LISTING

<160> NUMBER OF SEQ ID NOS: 1

<210> SEQ ID NO 1
<211> LENGTH: 42
<212> TYPE: DNA
<213> ORGANISM: Artificial Sequence
<220> FEATURE:
<223> OTHER INFORMATION: Corresponding DNA of Mic A sRNA

<400> SEQUENCE: 1
catctctgaa ttcagggatg atgataacaa atgcgcgtct tt                                    42

IMMUNOMODULATOR FOR HYPERSENSITIVITY REACTION TO HOUSE DUST MITE-DERIVED ALLERGEN

REFERENCE TO SEQUENCE LISTING

The present application is filed along with a Sequence Listing in electronic format. The Sequence Listing is provided as a file entitled 29257141_1.TXT, created Dec. 17, 2018, which is approximately 573 bytes in size. The information in the electronic format of the Sequence Listing is incorporated herein by reference in its entirety.

TECHNICAL FIELD

The present invention relates to an immunomodulator for preventing or treating an allergic disease caused by house dust mite-derived allergens, more specifically, a pharmaceutical composition comprising a bacteria-derived extracellular vesicle comprising house dust mite-derived allergens and a method for preparing thereof.

BACKGROUND ART

Atopy is a syndrome in which an excessive immune response (hypersensitivity) occurs to harmless antigens (allergens) commonly exposed, and the disease caused by it is atopic disease. Atopic dermatitis, allergic rhinitis, allergic conjunctivitis, allergic asthma and other atopic diseases frequently occur in people with atopic diseases. There is at least an allergic reaction of type 1 hypersensitivity associated with the immunological pathogenesis of atopy. Although atopy is defined in a variety of ways, it is characterized by a high level of IgE to allergens in the blood.

Allergy is defined as a condition in which an acquired immune response occurs in the body when exposed to the surrounding antigen, and the immune response changes during repeated exposure to the antigen as a memory for the antigen. The allergic phenomena that occur when exposed to harmful antigens have a beneficial effect on our body and induce an immune response through the vaccine. On the other hand, if an immune response to an harmless antigen is excessively induced and an hypersensitivity reaction occurs, an inflammatory reaction occurs in our body to cause an allergic disease. Asthma is a disease characterized by chronic inflammation of the airways. It is a disease in which asthma, dyspnea and other symptoms occur due to structural changes due to inflammation and functional changes. As a etiology of chronic inflammation seen in asthma, hypersensitivity to allergens in the surrounding environment is an important immune mechanism, especially hypersensitivity to allergens derived from house dust mite is known to be an important cause of asthma.

House dust mite is animals belonging to Arthropods inhabited by human habitation. House dust mite eats human scale and live in large quantities in urban house bed mattresses, carpets, furniture, etc., and are known to be the most important allergens in the world, the cause of allergic diseases such as allergic asthma. The digestive organs of house dust mite have various digestive enzymes, which spread to the air through stools excreted from house dust mite. When they are inhaled, hypersensitivity occurs in people with atopic asthma, and repeated exposure to house dust mite allergens Sneezing, rhinitis symptoms such as runny nose, asthma symptoms such as wheezing, difficulty in breathing, and atopic dermatitis such as itching. European house dust mite (*Dermatophagoides pteronyssinus*) and North American house dust mite (*Dermatophagoides farinae*) are common examples of important house dust mite that causes allergic diseases. Der p1, Der p2, Der p3, Der p4, Der p6, Der p9, and Der p15 are known as European house dust mite allergens. Der f1, Der f2, Der f11, and Der f18 are allergens derived from North American house dust mite which is known to be important. According to the results of domestic epidemiological studies, allergens derived from North American house dust mite is mainly present in indoor dusts in large cities, rather than European house dust mite, and Der f2 allergens have been reported to be the most abundant in indoor dust among the allergens derived from North American house dust mite (Son Jong Ryul et al. A Survey of Mite Allergens Contamination in House. Journal of Korean Society for Atmospheric Environment 2006; 22(5):719-23)

Immunotherapy can be classified as active immunotherapy, which induces disease-causing antigenic substances directly into the body to induce immune cell activity in the body, and passive immunotherapy that regulates the immune response by administering materials prepared in vitro, such as monoclonal antibodies Immune therapy. Active immunotherapy has been recognized as a more effective method in terms of cost and frequency of administration compared to passive immunotherapy as a method to prevent disease. Active immunotherapy is to induce defense immunity by using a strategy to induce acquired immune responses with the ability to induce antigen-specific long-term defense memory, which is characteristic of acquired immunity. The key to controlling allergic reactions is controlling allergen-specific immunological hypersensitivity reactions to allergens such as humoral (or antibody-mediated) and cellular (T-cell mediated) immunity.

Extracellular vesicles (EVs) secreted by bacteria are spherical phospholipid bilayers with a diameter of 20-100 nm. Biochemical and proteomic studies have shown that the outer membrane protein, lipopolysaccharide (LPS), outer membrane lipid, DNA, RNA, and proteins in the cytoplasm. Recently, there have been reports that Gram-negative bacteria such as *Neisseria meningitidis, Acinetobacterbaumannii, Porphyromonas gingivalis, Salmonella enterica, serovarTyphimurium, Helicobacter pylori*, and Vibriocholerae secrete extracellular vesicles to induce defense immunity against bacteria infections, and Gram-positive bacteria such as *Staphylococcus aureus* are also able to inhibit bacteria infection through extracellular vesicles to induce defense immunity against bacteria infections.

The vesicles derived from Gram-negative bacteria as antigen carriers have a problem of inducing serious toxicity such as sepsis despite its excellent immunity inducing effect. This is due to the presence of lipopolysaccharide (LPS), known as endotoxin, in the extracellular membrane of Gram-negative bacteria, which has recently been shown that inducing systemic vascular inflammation through TLR4 receptors present in large amounts in vascular endothelial cells, leading to sepsis. As a method for solving the problem of toxicity caused by Gram-negative bacteria-derived extracellular vesicles, a method of removing LPS present in extracellular vesicles or treating a compound inhibiting LPS activity may be used as an antigen carrier. The protoplast is a living cell material of plants or bacteria. By removing the extracellular membranes and cell walls of these cells by mechanical/enzymatic methods, the endotoxin content in the outer membrane of the bacteria are removed and the toxicity problem of the vesicles itself is solved. In addition, drugs such as polymyxin B can be treated to remove the activity of endotoxins present in extracellular vesicles.

Up to the present, allergen immunotherapy for house dust mite has been used mainly for the extraction of allergens from house dust mite or as a recombinant protein form, and there have been no cases in which allergens are expressed in antigen carriers such as extracellular vesicles.

Disclosure

Technical Problem

Accordingly, the present invention provides a pharmaceutical composition comprising a bacteria expressing allergens derived from house dust mite, extracellular vesicles derived therefrom, and a method for preparing the same thereof.

In addition, the present invention provides a method for controlling hypersensitivity caused by house dust mite allergens using the composition.

The objects of the present invention are not limited to those mentioned above, and other objects, advantages and features of the present invention should be clearly understandable by those skilled in the art from the following description.

Technical Solution

The present invention provides a pharmaceutical composition for preventing or treating an allergic disease comprising a bacteria-derived extracellular vesicle as an active ingredient, wherein the bacteria is overexpressed house dust mite-derived allergen gene, wherein the allergic disease is caused by house dust mite-derived allergens.

In one embodiment of the present invention, the bacteria is *E. coli* or *Salmonella* spp.

In another embodiment of the present invention, the house dust mite is European house dust mite (*Dermatophagoides pteronyssinus*) or North American house dust mite.

In still another embodiment of the present invention, the house dust mite-derived allergen is selected from the group consisting of Der p1, Der p2, Der p3, Der p4, Der p6, Der p9, Der p15, Der f1, Der f2, Der f11, and Der f18.

In addition, the present invention provides a method of preparing bacteria-derived vesicles for preventing or treating an allergic diseases caused by house dust mite-derived allergens the method comprising the following processes:
 (a) Overexpressing house dust mite-derived allergen gene in bacteria;
 (b) Culturing the bacteria in a culture medium;
 (c) Isolating bacteria-derived vesicles from the culture medium; and
 (d) Removing endotoxin in an outer membrane of the bacteria-derived vesicles In one embodiment of the present invention, the method of separating the bacteria-derived vesicles in the step (c) includes the steps of separating naturally secreted vesicles by filter method and/or ultracentrifugation method, or by making a vesicle by an artificial method, followed by performing filter method and/or ultracentrifugation method.

In another embodiment of the present invention, the method for removing the endotoxin in the step (d) includes the steps of removing the vesicle endotoxin (LPS, peptidoglycan, etc.) with lysozyme, or inhibiting the endotoxin (LPS) with a drug such as polymyxin B.

In still another embodiment of the present invention, the allergic disease caused by the house dust mite is selected from the group consisting of asthma, rhinitis and atopic dermatitis.

Further, the present invention provides an immunomodulator for preventing or treating allergic diseases caused by house dust mite, which comprises the bacteria-derived extracellular vesicles prepared by the method as an active ingredient.

In one embodiment of the present invention, the immunomodulator is that a house dust mite allergens (Der f2, etc.) are overexpressed in the lumen of bacteria-derived extracellular vesicles.

In still another embodiment of the present invention, the bacteria-derived vesicles may have an average diameter of 10-200 nm.

In addition, the present invention provides, a method for preventing or treating allergic diseases caused by house dust mite-derived allergens using bacteria-derived vesicles. Specifically, the present invention provides a method of preventing or treating an allergic disease comprising administering a pharmaceutical composition comprising an extracellular vesicle derived from bacteria as an active ingredient to a subject.

The bacteria may be overexpressed the allergen gene derived from house dust mite, and the allergic disease may be caused by house dust mite allergens.

In addition, the present invention provides the use of the bacteria-derived extracellular vesicles for preventing or treating an allergic diseases caused by house dust mite-derived allergens.

The bacteria may be overexpressed the allergen gene derived from house dust mite, and the allergic disease may be caused by house dust mite allergens.

Advantageous Effects

The present invention uses a bacteria-derived vesicle comprising house dust mite allergen (Der f2, etc.) as an allergen immunomodulator derived from house dust mite to control hypersensitivity by allergens. Ultimately, allergic diseases caused by house dust mite can be effectively prevented or treated.

DESCRIPTION OF DRAWINGS

FIG. 1 shows a schematic diagram of how to make an immunomodulator obtained by cloning a *D. farinae* allergen (Der f2), loading it into *Escherichia coli*, treating it with lysozyme in a culturing process to make a protoplast, manufacturing an artificial extracellular vesicles by extrusion.

FIG. 2 shows a photograph of a Der f2 allergen-loaded extracellular vesicle taken by a transmission electron microscope.

FIG. 3 shows the result of measuring the size of Der f2 allergen-loaded extracellular vesicles by a dynamic light scattering method.

FIG. 4 shows the result of measuring the expression of a co-stimulatory molecule (CD86) by treating a Der f2 allergen-loaded extracellular vesicle with a bone marrow-derived dendritic cell.

FIG. 5 shows the result of measuring the secretion amount of IL(interleukin)-12 and IL-6 by treating Der f2 allergen-loaded extracellular vesicles with bone marrow-derived dendritic cells.

FIG. 6 shows a schematic diagram of how to make an immunomodulator obtained by cloning small RNA present in bacteria, loading the cells into bacteria (*Salmonella typhimurium*), culturing the bacteria to separate extracellular vesicles, and then removing the lipopolysaccharide (LPS) activity in the outer of the vesicles by treating the polymyxin B (PMB)

FIG. 7 shows a diagram showing the morphological characteristics of extracellular vesicles derived from Mic A small RNA overexpressing strains by dynamic light scattering and electron microscopy.

FIG. 8 shows a diagram showing the amounts of separation of gamma interferon, IL-4 and IL-17 obtained by injecting the small RNA over-expression strain (*Salmonella typhimurium*) derived vesicles to abdominal cavity three times, and then stimulating immuno cells isolated from the local lymph node by anti-CD3/anti-CD28.

FIG. 9 shows a diagram showing the secretion amount of inflammatory mediator (IL-6, TNF-alpha) after administration of polymyxin B (PMB) at various concentrations in the course of administering the vesicles derived from Mic A small RNA overexpressing stain (*Salmonella typhimurium*) to the inflammatory cells (Macrophage cell line RAW264.7).

FIG. 10 shows a diagram showing the secretion amount of IL-6 after administrating of polymyxin B (PMB) at more detailed concentrations in the course of administering the vesicles derived from Mic A small RNA overexpressing stain (*Salmonella typhimurium*) to the inflammatory cells (Macrophage cell line RAW264.7).

FIG. 11 shows an experimental protocol for evaluating the immunogenicity of Der f2 allergen-loaded extracellular vesicles in mice.

IM: Intramuscular; IN: Intranasal; BAL: Bronchoalveolar Lavage

FIGS. 12A and 12B show the results of measuring the antigen-specific IgG antibody in the mouse serum and the ability to produce the antigen-specific IgA antibody in the bronchoalveolar lavage fluid after the Der f2 allergen-loaded extracellular vesicles were administered by the method of FIG. 11.

FIG. 13 shows the results of measurement of gamma-interferon, IL-17, IL-4 and IL-10 after administration of Der f2 allergen-loaded extracellular vesicles by the method of FIG. 6 followed by isolating T cells from mouse lung tissue followed by stimulating with anti-CD3/CD28.

FIG. 14 shows a protocol for evaluating the immunomodulatory effect of Der f2 allergen-loaded extracellular vesicles in a mouse asthma model induced by North American house dust mite extract antigen and aluminum hydroxide (alum).

IM: Intramuscular; IN: Intranasal; IP: Intraperitoneal

FIG. 15 shows the results of evaluating the anti-inflammatory effect of the Der f2 allergen-loaded extracellular vesicles in the house dust mite allergen-induced mouse asthma model by the number of inflammatory cells in the bronchoalveolar lavage fluid.

MODES OF THE INVENTION

In order to develop an antigen-specific immunomodulator, it is important to select an antigen and an adjuvant to induce a desired immune response. In the present invention, Der f2 allergen, which is the most abundant immunomodulator candidate antigen in korea to control hypersensitivity to house dust mite allergen, was targeted.

On the other hand, based on the fact that the extracellular vesicles derived from bacteria can induce various immune responses to the host, there have been attempts to use extracellular vesicles derived from bacteria as adjuvants, but the extracellular vesicles derived from bacteria have the LPS, peptidoglycan and the like, so there is a problem that the problem of toxicity due to extracellular vesicles must be solved. Accordingly, in the present invention, in order to eliminate the toxicity problem of the extracellular vesicles when using the extracellular vesicles derived from bacteria as a drug delivery vehicle, the outer membrane of the extracellular vesicles and the cell wall comprising the peptidoglycan layer was removed to prepare a protoplast, and artificial extracellular vesicles were prepared and used. We also tried to reduce toxicity by co-administration of polymyxin B, which inhibits the activity of LPS present in the vesicle outer membrane, to naturally secreted vesicles after culturing the bacteria.

Specifically, in the present invention, a Der f2 antigen, which is a major allergen derived from North American house dust mite, is overexpressed in *E. coli* and then cultured. Then, protoplasts were prepared by treating lysozyme, and extracellular vesicles were prepared by extrusion method to prepare candidate substances. In addition, in order to optimize the vaccine candidates, cloning Mic A small RNA present in bacteria, inserting into *Salmonella* and overexpressed, and then cultured. Then, PMB was administered simultaneously with vesicle, establishing the optimal concentration by reducing toxicity while maintaining immunogenicity.

Subsequently, the immunogenicity of the antigen-loaded candidate extracellular vesicles was assessed in vitro and in vivo to determine the route of administration and dosage for efficacy evaluation. As a result, it was found that the antigen-loaded extracellular vesicles were an effective vaccine.

In addition, in order to evaluate the efficacy of the immunomodulator in the disease model, North American house dust mite extract and alum were injected into the peritoneal cavity and sensitized with allergen, and then the mite extract solution alone was administered to the nasal cavity to prepare an asthmatic animal model.

In the present invention, the 'house dust mite allergy disease' is not particularly limited as long as it is a disease that can be caused by house dust mite allergens, but is preferably selected from the group consisting of asthma, rhinitis and atopic dermatitis.

In the present invention, 'treating or preventing a allergic disease' includes alleviating and mitigating a allergic disease, and improving symptoms, and also, includes lowering the probability of getting a allergic disease.

In the present invention, the bacteria capable of overexpressing the gene is not particularly limited, but is preferably *E. coli* or *Salmonella* spp.

In the present invention, in the step of separating extracellular vesicles, naturally secreted extracellular vesicles can be used. There is no particular limitation on the method for separating extracellular vesicles, but it can be obtained by concentration with a filter followed by ultracentrifugation and the like.

In the present invention, an extracellular vesicle can be artificially prepared, and the method for preparing the vesicle is not particularly limited, but it can be obtained by extrusion with a filter, and further includes a process such as centrifugation and ultracentrifugation.

In the present invention, a method for isolating the extracellular vesicle from the culture medium is not specifically limited as long as extracellular vesicles are included. For example, extracellular vesicles may be isolated from a bacteria culture medium or a fermented food using a method such as centrifugation, ultracentrifugation, filtration with a filter, gel filtration chromatography, free-flow electrophoresis, capillary electrophoresis, isolation using a polymer, or a combination thereof. In addition, processes such as washing for removing impurities and concentration of obtained extracellular vesicles may be further included. The extracellular vesicles include extracellular vesicles naturally or artificially secreted.

In the present invention, the allergens derived from house dust mite is expressed in the lumen of the extracellular vesicles prepared by the above method. Der f2, Der p2 and the like are preferred as expressed proteins, and Der f2 is most preferable.

In the present invention, the extracellular vesicles prepared by the method may have an average diameter of 10 to 200 nm, and preferably, 20 to 100 nm.

In the present invention, the composition for treating or preventing a allergic disease may be prepared into a pharmaceutical composition. In order to use the composition for treatment and prevention, it is possible to administer extracellular vesicles according to the present invention themselves, but it is preferable that the pharmaceutical composition comprising the extracellular vesicles as an active ingredient.

The pharmaceutical composition comprising the isolated extracellular vesicles as an active ingredient and may include a pharmaceutically acceptable carrier. The pharmaceutically acceptable carrier that can generally be used in formulation includes saline, sterile water, Ringer's solution, buffered saline, cyclodextrins, a dextrose solution, a maltodextrin solution, glycerol, ethanol, a liposome, and the like, but the present invention is not limited thereto. As necessary, other conventional additives such as an antioxidant, a buffer, etc. may be further included. Also, a diluent, a dispersant, a surfactant, a binder, a lubricant, and the like may be further added to prepare the composition into an injectable formulation such as an aqueous solution, a suspension, an emulsion, etc., a pill, a capsule, a granule, or a tablet. A suitable pharmaceutically acceptable carrier and a preparation thereof may be preferably referenced from the method disclosed in the Remington's document (Remington's Pharmaceutical Science, Mack Publishing Company, Easton Pa.) according to a component. The pharmaceutical composition according to the present invention is not limited to a formulation, but may be prepared into injections, inhalations, skin remedies for external use, and the like.

A method for administering a pharmaceutical composition according to the present invention is not specifically limited, but may include parenteral administration such as intramuscular injection, subcutaneous, inhalation, nasal cavity, hypoglossal, dermal application, or oral administration depending on a desired method.

A dose range may vary depending on weight, age, gender, and health condition of a patient, a diet, the duration of administration, an administration mode, an excretion rate, severity of disease, and the like. A dose used daily refers to a sufficient amount of the therapeutic substance of the present invention, which is administered to a subject requiring treatment so as to alleviate a disease. An effective dose of the therapeutic substance may vary depending on a specific compound, the state and severity of a disease, and a subject that requires treatment and may be generally determined by skilled practitioners. As a non-limiting example, a dose of the composition according to the present invention for a human body may vary depending on age, weight, and gender of a patient, an administration mode, health condition, and the severity of disease.

Hereinafter, preferred exemplary examples of the invention will be described for promoting understanding of the present invention. However, the following examples should be considered in a descriptive sense only, and the scope of the invention is not limited to the examples.

EXAMPLES

Example 1: Preparation of Der f2 Antigen Loaded Extracellular Vesicles (See FIG. 1)

Der f2 gene (reference sequence: GeneBank AB195580) was synthesized for cDNA by RT-PCR method for Der f2 cloning, a major allergen of North American house dust mite. The PCR product was inserted into a T-blunt PCR cloning kit (Solgent) and each plasmid was cleavaged with EcoRI (OmpA, ABC transporter) and BglII (FepA). The fragments were separated by electrophoresis, inserted into pET-30a plasmid, transformed into *Escherichia coli* DH5a by thermal shock method, and finally cloning the gene.

The Der f2 clone obtained in the above example was cultured in Luria Bertani broth (Merch) at 37° C., 200 rpm for 12 hours, and then Expre plasmid mini prep. Kit (GeneAll) was used to isolate each plasmid and transfected into *E. coli* BL21 (Real Biotech).

The BL21 was cultured in 100 ml LB broth (1 mM IPTG) for 3 hours at 200 rpm and 37° C. until the OD value reached 0.3, and the bacteria pellet obtained by centrifugation at 3,000×g for 10 minutes at 4° C. was washed with Tris (0.01 M Tris HCl, 0.5 M sucrose), centrifuged at 3,000×g for 10 min at 4° C., and resuspended in Tris buffer. Resuspended bacteria were treated with 0.01 M EDTA at 100 rpm for 30 min at 37° C., pelleted at 4° C., 3,000×g for 10 min, and then washed with Tris buffer for pelleting.

Next, the bacteria pellet was resuspended in Tris buffer and treated with 1 mg/ml lysozyme (Sigma) at 37° C., 100 rpm for 2 hours to obtain protoplasts, and then extruded through a membrane with a pore size of 10 μM, 5 μM, and 1 μM through in order with a LiposoFast extruder (Avestin). Finally, Der f2 antigen-loaded extracellular vesicles were obtained by ultracentrifugation with 10% and 50% opti-prep density gradient media (OptiPrep).

Example 2: Physical Properties of Der f2 Antigen-Loaded Extracellular Vesicles

Der f2 antigen-loaded extracellular vesicles obtained in Example 1 were diluted with PBS (50 μg/ml) and loaded with 10 μl into 300-mesh copper grids (EMS). Uranyl acetate (2%) was dropped onto the grid for negative staining and observed with a JEM1011 electron microscope (JEOL). As a result, as shown in FIG. 2, it was confirmed that the extracellular vesicles were spherical and surrounded by a lipid bilayer.

In order to measure the size of the Der f2 antigen-loaded extracellular vesicles obtained in Example 1, the extracellular vesicles were diluted with PBS (500 ng/ml) and the diameter size distribution was measured by dynamic light scattering using a Zetasizer Nano ZS (Malvern Instruments) and the result analyzed by using Dynamic V6 software. As a result, as shown in FIG. 3, it was found that the diameter of the extracellular vesicles was 100-300 nm.

Example 3: Innate Immune Response by Der f2 Antigen Loaded Vesicles

Der f2 antigen-loaded extracellular vesicles should be able to induce an immune response in order to utilize the extracellular vesicles as an immunomodulator. Therefore, in order to evaluate the level of induction of innate immune response by Der f2 antigen-loaded extracellular vesicles, In vitro experiments were performed using dendritic cells (bone marrow-derived dendritic cells, BMDC).

First, BMDC ($5 \times 10^5$ cells/well) was cultured in DMEM comprising 10% FBS and antibiotics (100 units/ml penicillin and 100 μg/ml streptomycin) for 24 hours at 37° C. in 24 well tissue culture plates (TPP). After removal of the medium, Der f2 antigen-loaded extracellular vesicles were replaced with serum-free DMEM medium supplemented with 0.1 and 1 ug/ml. After 15 hours, the expression level of IL-12 and IL-6, which are T cell differentiation cytokines, was measured by the degree of CD86 expression in BMDC and the ELISA assay using the culture medium.

As a result, as shown in FIG. 4, expression of CD86 in antigen-presenting cells was greatly increased by the Der f2 antigen-loaded extracellular vesicles (see FIG. 4). In addition, as shown in FIG. 5, the antigen-presenting cells treated with Der f2 antigen-loaded extracellular vesicles significantly increased IL-12 secretion important for differentiation into Th1 cells. and significantly increased IL-6 secretion important for differentiation into Th17 cells (FIG. 5).

Example 4: Physical Analysis of Vesicles Derived from MicA sRNA Overexpressing Strains A pBRplac-sRNA plasmid comprising the same Mic A sRNA as the *Escherichia coli* sRNA base sequence was introduced into *Salmonella* using an sRNA having excellent conservation of Hfq-binding sRNA. The corresponding DNA sequence of Mic A sRNA is CATCTCTGAAT-TCAGGGATGATGATAACAAATGCGCTTCTTT (SEQ ID NO: 1). Specifically, pBRplac-sRNA was introduced into *Salmonella Typhimurium* 140285 species by electroporation.

In the above example, the sRNA over-expression strain was cultured in vitro, and the vesicles were separated and the physical properties of the vesicles were confirmed by dynamic light scattering and transmission electron microscopy. As a result, as shown in Table 1 and FIG. 7, it was confirmed that the extracellular vesicles derived from Mic A sRNA-overexpressing strains were about 20 nm in size similar to the control group, pBRplac, and had similar shapes (FIG. 7).

TABLE 1

| Strain(sRNA) | Average size(nm) |
| --- | --- |
| *Salmonella typhimurium*(pBRplac) | 26.07 ± 5.98 |
| *Salmonella typhimurium*(RseX) | 19.93 ± 2.503 |
| *Salmonella typhimurium*(MicA) | 21.39 ± 1.92 |

Example 5: Immunogenicity of Vesicles Derived from *Salmonella* Overexpressing Mic a sRNA

*Salmonella* strains are known to induce enteritis and induce Th1 immune response. Thus, the ability of the extracellular vesicles obtained from sRNA overexpression to induce Th1 immune response was confirmed. Specifically, 5 mice per group (C67BL/6) received 100 ug/hd of extracellular vesicles through the abdominal cavity at 2-day intervals. On the 5th day, the cells were dissected from the lymph node of the peritoneal cavity, and T-cell re-stimulation was performed for 12 hours using anti-CD3 and CD28, and the amount of cytokine secreted from the T cells was measured.

As a result, as shown in FIG. 8, the cytokines IFN-γ and IL-17 associated with the Th1 and Th17 immunoreactivity were increased when the extracellular vesicles derived from the sRNA-overexpressing strains were administered, compared with the control group, and the cytokines related to the Th2 immune response IL-4 was not different from the control group when the extracellular vesicles derived from the sRNA-overexpressing strain were administered (FIG. 8). Through this, it was confirmed that Th1 and Th17 immunoreactivity similar to live bacteria infection can be induced by using extracellular vesicles derived from *Salmonella* strains overexpressing sRNA.

Example 6: Optimization of Vesicles Derived from *Salmonella* Overexpressing Mic a sRNA

*Salmonella*-derived vesicles themselves have good immunogenicity, but toxicity due to LPS present in the extracellular membrane is a problem. In order to solve this problem, the induction level of innate immune response was evaluated by mixing PMB inhibiting the activity of LPS with vesicles derived from *Salmonella* overexpressing Mic A sRNA.

Specifically, inflammatory cells (macrophage RAW264.7, $5 \times 10^5$ cells/well) were cultured in DMEM comprising 10% FBS and antibiotics (100 units/ml penicillin and 100 μg/ml streptomycin) for 24 hours at 37° C. 24 well tissue culture plate (TPP). After the medium was removed, extracellular vesicles comprising PMB were changed to serum-free DMEM medium added at a concentration of 1 ug/ml. After 15 hours, secretion of IL-6 and TNF-alpha was measured in inflammatory cells.

As a result, as shown in FIG. 9, IL-6 secretion decreased when extracellular vesicles were mixed at a concentration of PMB 1 μg/ml or 10 μg/ml and administered. and the amount of TNF-alpha separation was inhibited by the concentration of 10 μg/ml of PMB. This means that the optimal PMB dilution concentration for vesicles prepared by the above method is between 1 ug/ml and 10 ug/ml.

In order to determine the optimum PMB dilution concentration, in the above method, the PMB concentration was subdivided into 1, 2, 4, 8, and 10 ug/ml and administered to the macrophages together with the vesicles. As a result, it was found that the secretion of IL-6 in the macrophages no longer decreased above the concentration of 2 ug/ml, and thus it was confirmed that the candidate substance could be optimized by diluting PMB concentration (FIG. 10).

Example 7: Antibody Immune Response by Der f2 Antigen Loaded Vesicle

In order to confirm the ability of the Der f2 antigen-loaded extracellular vesicles to induce antibody immunoreactivity in vivo and to determine the effective amount of Der f2 antigen loaded extracellular vesicles, Der f2 antigen loaded extracellular vesicles were administered to mice to induce immunity. In addition, Der f2 specific IgG antibody was measured by collecting blood from a mouse to which a control (PBS) and a Der f2 antigen-loaded extracellular vesicle were administered after induction of an immune response, and a bronchoalveolar lavage fluid was collected and the concentration of Der f2 specific sIgA antibody was measured.

Specifically, 100 μl of PBS comprising 100 ng Der f2 was coated on a 96-well black plate (Greiner Bio-one) at 4° C. for 24 hours. The plate coated with Der f2 was washed with PBS, treated with 1% BSA solution diluted with PBS for 1 hour, and then blocked and washed again with PBS.

Serum was separated from blood, serum, and cell layers from mice administered with control (PBS) and Der f2 antigen-loaded extracellular vesicles. After separating the cell layer and supernatant from the bronchoalveolar lavage fluid, The serum and supernatant were diluted with 1% BSA solution and reacted on a plate coated with Der f2 antigen for 2 hours.

After incubation, the plates were washed and incubated for 2 hours with 200 ng/ml horseradish peroxidase-conjugated goat anti-mouse IgG and IgA (Santa Cruz Biotechnology). After washing the plate again, ECL substrate (Thermo Scientific) was added and the titers of IgG and sIgA antibodies were analyzed using a Victor Wallac 1420 apparatus (PerkinElmer).

As a result, as shown in FIG. 11, the mouse serum that induced the immune response by intramuscular injection comprising Der f2 antigen-loaded extracellular vesicles was increased Der f2 antigen-specific IgG antibody production irrespective of whether administering in nasal cavity with extracellular vesicles. On the other hand, Der f2 antigen-specific sIgA production in bronchoalveolar lavage fluid increased only when intramuscular injection of Der f2 antigen-loaded extracellular vesicles was followed by nasal administration (FIG. 12A and FIG. 12B).

Example 8: T Cell Immune Response by Der f2 Antigen Loaded Extracellular Vesicles In vivo, the Der f2 antigen-loaded extracellular vesicles were administered to induce an immune response, and then, T cell responses were assessed by measuring the amount of cytokine produced in T cells in mice administered with control (PBS) and Der f2 antigen loaded extracellular vesicles.

In other words, the extracted lung tissue was resolved by passing it through a 100 μm cell strainer (BD Biosciences) in a 5 ml syringe washing buffer (DMEM comprising 2.5% FBS and 0.01 M HEPES). The separated cells were treated with ammonium chloride solution (STEM CELL) at 4° C. for 10 minutes to allow the red blood cells to cytolysis. The cells were washed with washing buffer and filtered with a 40 μm cell strainer (BD), and then, cultured in a 24-well plate for 12 hours using RPMI 1640 medium comprising 10% FBS, 50 μM 2-ME, 0.01 M HEPES and antibiotics (100 units/ml penicillin, 100 μg/ml streptomycin). At this time, 24-well plates were coated with 1 μg/ml anti-CD3 (eBioscience) and 1 μg/ml anti-CD28 (eBioscience) antibody to re-stimulate T cells.

As a result, as shown in FIG. 13, the amount of IFN-γ, which is a major cytokine produced by Th1 cells, was increased in the Der f2 antigen-loaded extracellular vesicle treated group compared to the control. and Der f2 antigen-loaded extracellular vesicles dose-dependently decreased upon nasal administration. In the case of IL-17, a major cytokine produced in Th17, the Der f2 antigen-loaded extracellular vesicle administration group was increased in comparison with the control group regardless of nasal administration (FIG. 13).

Example 9: Anti-Inflammatory Effect of Der f2 Antigen Loaded Extracellular Vesicles in an Allergen-Induced Asthmatic Animal Model Extracted from North American House Dust Mite To evaluate the efficacy of Der f2 antigen loaded extracellular vesicles in a house dust mite allergen-induced mouse asthma model, the following experiment was performed (see FIG. 14). As shown in FIG. 14, allergens were extracted from North American house dust mite to prepare an asthma model, and then alum were mixed with 75 μg of allergens and administered twice a day to the abdominal cavity, followed by administration of 50 μg of allergens alone to the nasal cavity twice to prepare an asthma model (FIG. 14).

In order to induce an immune response with the Der f2 antigen-loaded extracellular vesicles, Der f2 antigen-loaded extracellular vesicles were pretreated three times in intramuscular injection and nasal administration before preparing the asthma model, as shown in FIG. 9 at the concentrations set by the method of Example 5. And during the preparation of the asthma model, only the Der f2 antigen-loaded extracellular vesicles were administered to the nasal cavity (FIG. 14).

As a result, as shown in FIG. 15, when the positive control mice that did not administered Der f2 antigen-loaded extracellular vesicles, the number of inflammatory cells in the bronchoalveolar lavage fluid was significantly increased when asthma was induced by house dust mite allergens. The number of inflammatory cells in the bronchoalveolar lavage fluid of the mice induced with the Der f2 antigen loaded extracellular vesicles before the asthma model was significantly reduced compared to the positive control. Mice administered with the Der f2 antigen-loaded extracellular vesicles before and after the modeling of the asthma model had a significantly reduced inflammatory cells compared to the positive control group, as well as the extracellular vesicles loaded with the Der f2 antigen administrated prior to the modeling of the asthma model (FIG. 15).

Therefore, when the Der f2 antigen loaded extracellular vesicles were administered to the nasal passages, it was found that effectively suppressing asthma caused by North American house dust mite.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

The present invention uses a bacteria-derived vesicle comprising house dust mite allergen (Der f2, etc.) as an allergen immunomodulator derived from house dust mite to control hypersensitivity by allergens. Ultimately, allergic diseases caused by house dust mite can be effectively prevented or treated.

The invention claimed is:

1. A method of inducing defense immunity to at least one mite allergen, the method comprising:
 administering, to a subject, a composition comprising bacteria-derived extracellular vesicles loaded with at least one mite allergen in an amount sufficient to induce defense immunity to the at least one mite allergen in the subject,
 wherein the bacteria-derived extracellular vesicles loaded with the at least one mite allergen comprise isolated extracellular vesicles of bacteria transformed with at least one gene configured to express the at least one mite allergen,
 wherein an outer membrane of the isolated extracellular vesicles comprises endotoxin,
 wherein the composition further comprises an effective amount of a drug inhibiting toxicity of the endotoxin,
 wherein the composition is administered to the subject multiple times, and
 wherein the multiple times comprise at least one intramuscular injection followed by at least one nasal administration.

2. The method of claim 1, wherein the at least one mite allergen comprises an allergen of North American house dust mite (*Dermatophagoides farinae*) or European house dust mite (*Dermatophagoides pteronyssinus*), wherein the drug inhibiting toxicity of the endotoxin comprises polymyxin B.

3. The method of claim 1, wherein the at least one mite allergen comprises one or more allergens selected from the group consisting of Der f1, Der f2, Der f11, and Der f18 of North American house dust mite (*Dermatophagoides farinae*).

4. The method of claim 1, wherein the at least one mite allergen comprises one or more allergens selected from the group consisting of Der p1, Der p2, Der p3, Der p4, Der p6, Der p9, and Der p15 of European house dust mite (*Dermatophagoides pteronyssinus*).

5. The method of claim 1, wherein the at least one mite allergen comprises allergen Der f2 of North American house dust mite (*Dermatophagoides farinae*), wherein the drug inhibiting toxicity of the endotoxin comprises polymyxin B.

6. The method of claim 1, wherein the multiple times of administering comprise administering prior to occurrence of an allergic condition in the subject.

7. The method of claim 1, wherein the multiple times of administering comprise administering both prior to and subsequent to occurrence of an allergic condition in the subject.

8. The method of claim 7, wherein administering subsequent to the allergic condition is by nasal administration.

9. The method of claim 1, wherein the bacteria are *E. coli* or *Salmonella*.

10. The method of claim 1, wherein the at least one mite allergen comprises allergen Der f2 of North American house dust mite, wherein:
 the bacteria-derived extracellular vesicles loaded with allergen Der f2 comprise isolated extracellular vesicles of bacteria transformed with a gene configured to express the allergen Der f2,
 inducing defense immunity addresses an inflammatory disease of airways in the subject, wherein the composition is administered by at least one of intramuscular injection and nasal administration,
 the composition is administered to the subject multiple times, and
 the multiple times comprise at least one intramuscular injection followed by at least one nasal administration.

11. The method of claim 10, wherein the multiple times of administering comprise administering prior to occurrence of an asthmatic condition in the subject.

12. The method of claim 10, wherein the multiple times of administering comprise administering both prior to and subsequent to occurrence of an asthmatic condition in the subject.

13. The method of claim 12, wherein administering subsequent to the asthmatic condition is by nasal administration.

14. The method of claim 10, wherein the bacteria are *E. coli* or *Salmonella*.

15. The method of claim 1, wherein the at least one mite allergen comprises allergen Der f2 of North American house dust mite,
 wherein the bacteria-derived extracellular vesicles loaded with allergen Der f2 comprise isolated extracellular vesicles of bacteria transformed with a gene configured to express the allergen Der f2,
 wherein the bacteria-derived extracellular vesicles loaded with allergen Der f2 are administered at least once prior to occurrence of an asthmatic condition and further administered at least once subsequent to occurrence of the asthmatic condition, wherein administering at least once subsequent to occurrence of the asthmatic condition comprises nasal administration.

16. A method of inducing defense immunity to at least one mite allergen, the method comprising:
 administering, to a subject, a composition comprising bacteria-derived extracellular vesicles loaded with at least one mite allergen in an amount sufficient to induce defense immunity to the at least one mite allergen in the subject, wherein the bacteria-derived extracellular vesicles loaded with the at least one mite allergen comprise isolated extracellular vesicles of bacteria transformed with at least one gene configured to express the at least one mite allergen, wherein an outer membrane of the isolated extracellular vesicles comprises endotoxin, wherein the composition further comprises an effective amount of a drug inhibiting toxicity of the endotoxin, wherein the composition is administered to the subject multiple times, wherein the multiple times of administering comprise at least one intramuscular injection and at least one nasal administration.

17. The method of claim 10, wherein the inflammatory disease of airways is asthma.

* * * * *